(12) United States Patent
Peckham et al.

(10) Patent No.: US 7,963,988 B2
(45) Date of Patent: Jun. 21, 2011

(54) EPTFE LAMINATION—RESIZING EPTFE TUBING

(75) Inventors: John Peckham, Sunnyvale, CA (US); Frank A. Musbach, Pleasanton, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 151 days.

(21) Appl. No.: 11/159,613

(22) Filed: Jun. 23, 2005

(65) Prior Publication Data
US 2006/0293744 A1 Dec. 28, 2006

(51) Int. Cl.
A61F 2/06 (2006.01)
A61F 2/82 (2006.01)

(52) U.S. Cl. ............ 623/1.29; 623/1.13; 623/1.32; 623/1.34

(58) Field of Classification Search ........... 623/1.13, 623/1.22, 1.25, 1.27–1.29, 1.34, 1.11, 1.12, 623/1.23, 1.32–1.33
See application file for complete search history.

(56) References Cited

U.S. PATENT DOCUMENTS

| | | | |
|---|---|---|---|
| 4,503,569 A | 3/1985 | Dotter | |
| 4,580,568 A | 4/1986 | Gianturco | |
| 4,732,152 A | 3/1988 | Wallstén et al. | |
| 4,733,665 A | 3/1988 | Palmaz | |
| 4,856,516 A | 8/1989 | Hillstead | |
| 4,886,062 A | 12/1989 | Wiktor | |
| 5,047,050 A * | 9/1991 | Arpesani | 623/1.34 |
| 5,562,725 A | 10/1996 | Schmitt et al. | |
| 5,593,417 A | 1/1997 | Rhodes | |
| 5,735,892 A | 4/1998 | Myers et al. | |
| 5,810,870 A | 9/1998 | Myers et al. | |
| 5,925,075 A | 7/1999 | Myers et al. | |
| 5,993,489 A | 11/1999 | Lewis et al. | |
| 6,176,875 B1 * | 1/2001 | Lenker et al. | 623/1.49 |
| 6,217,609 B1 * | 4/2001 | Haverkost | 623/1.13 |
| 6,264,690 B1 | 7/2001 | Von Oepen | |
| 6,352,561 B1 | 3/2002 | Leopold et al. | |

(Continued)

FOREIGN PATENT DOCUMENTS

EP 0 893 108 A2 1/1999

(Continued)

OTHER PUBLICATIONS

PCT Notification of Transmittal of the International Search Report and the Written Opinion of the International Searching Authority, or the Declaration for International Application No. PCT/US2006/024372, Oct. 30, 2006 (2 pages).

(Continued)

*Primary Examiner* — David Isabella
*Assistant Examiner* — Suba Ganesan
(74) *Attorney, Agent, or Firm* — Vidas, Arrett & Steinkraus, P.A.

(57) ABSTRACT

A vascular graft includes a vessel structure having outer and inner wall surfaces. The vessel structure has outer and inner transverse dimensions. The vascular graft includes a fold structure which is integral with the vessel structure. The fold structure extends from the outer or inner wall surface of the vessel structure for altering the inner or outer transverse dimension thereof. A method for making the vascular graft facilitates formation of the fold structure.

10 Claims, 8 Drawing Sheets

U.S. PATENT DOCUMENTS

| | | | |
|---|---|---|---|
| 6,383,171 B1 * | 5/2002 | Gifford et al. | 623/1.23 |
| 6,458,152 B1 * | 10/2002 | Khosravi et al. | 623/1.22 |
| 6,719,783 B2 | 4/2004 | Lentz et al. | |
| 6,786,920 B2 | 9/2004 | Shannon et al. | |
| 6,793,672 B2 | 9/2004 | Khosravi et al. | |
| 2002/0035396 A1 | 3/2002 | Heath | |
| 2003/0065345 A1 | 4/2003 | Weadock | |
| 2004/0030218 A1 * | 2/2004 | Kocur et al. | 623/1.13 |
| 2004/0049264 A1 | 3/2004 | Sowinski et al. | |

FOREIGN PATENT DOCUMENTS

| | | |
|---|---|---|
| WO | WO 00/45743 | 8/2000 |
| WO | WO 2005/018502 A1 | 3/2005 |

OTHER PUBLICATIONS

PCT International Search Report for International Application No. PCT/US2006/024372, Oct. 30, 2006 (5 pages).

PCT Written Opinion of the International Searching Authority for International Application No. PCT/US2006/024372, Oct. 30, 2006 (4 pages).

U.S. Appl. No. 10/830,787, filed Apr. 23, 2004, Rakos, USPTO Filing Receipt, specification and drawings.

U.S. Appl. No. 11/025,826, filed Dec. 28, 2004, Sherry, USPTO Filing Receipt, specification and drawings.

U.S. Appl. No. 11/025,571, filed Dec. 29, 2004, Sowinski, USPTO Filing Receipt, specification and drawings.

* cited by examiner

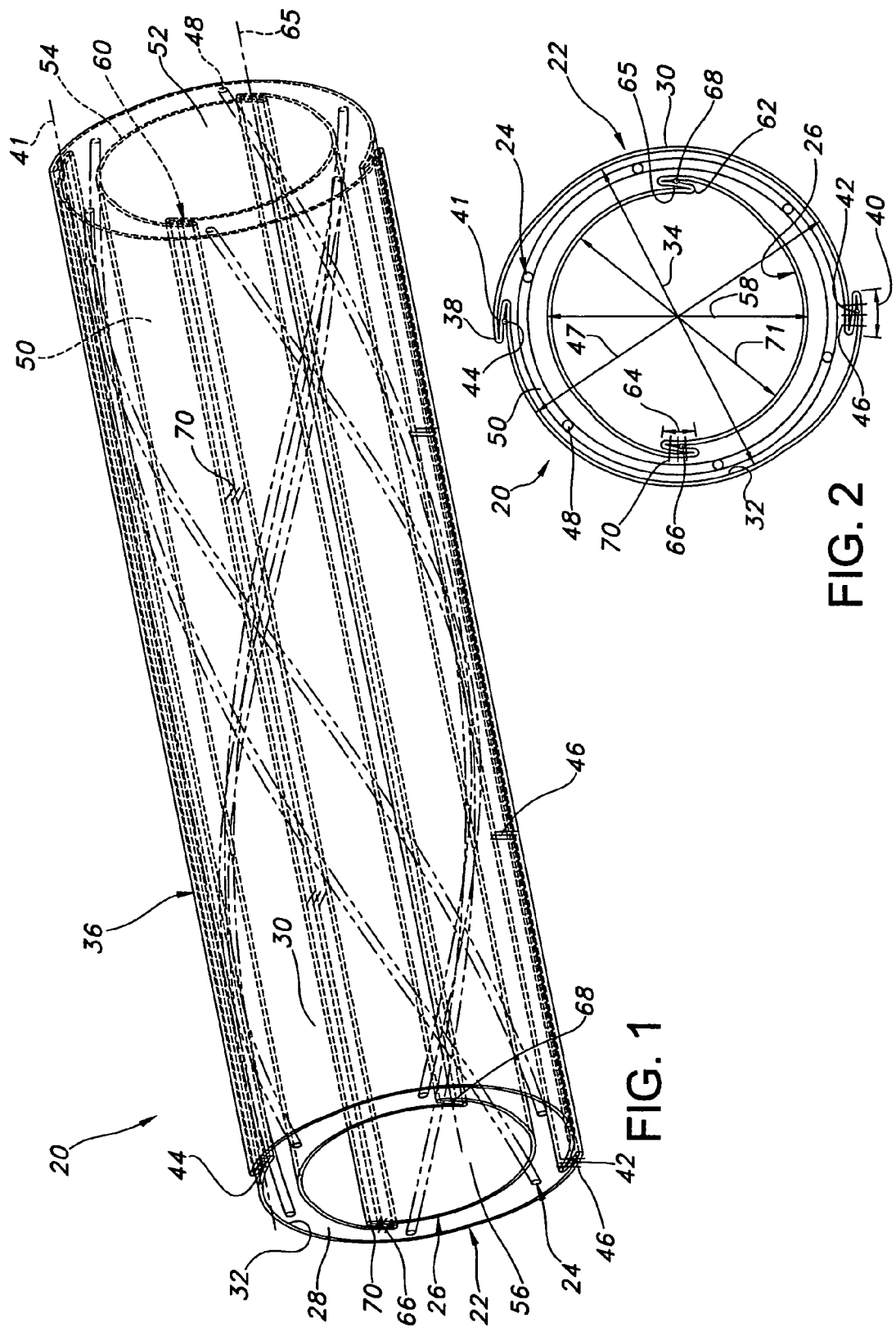

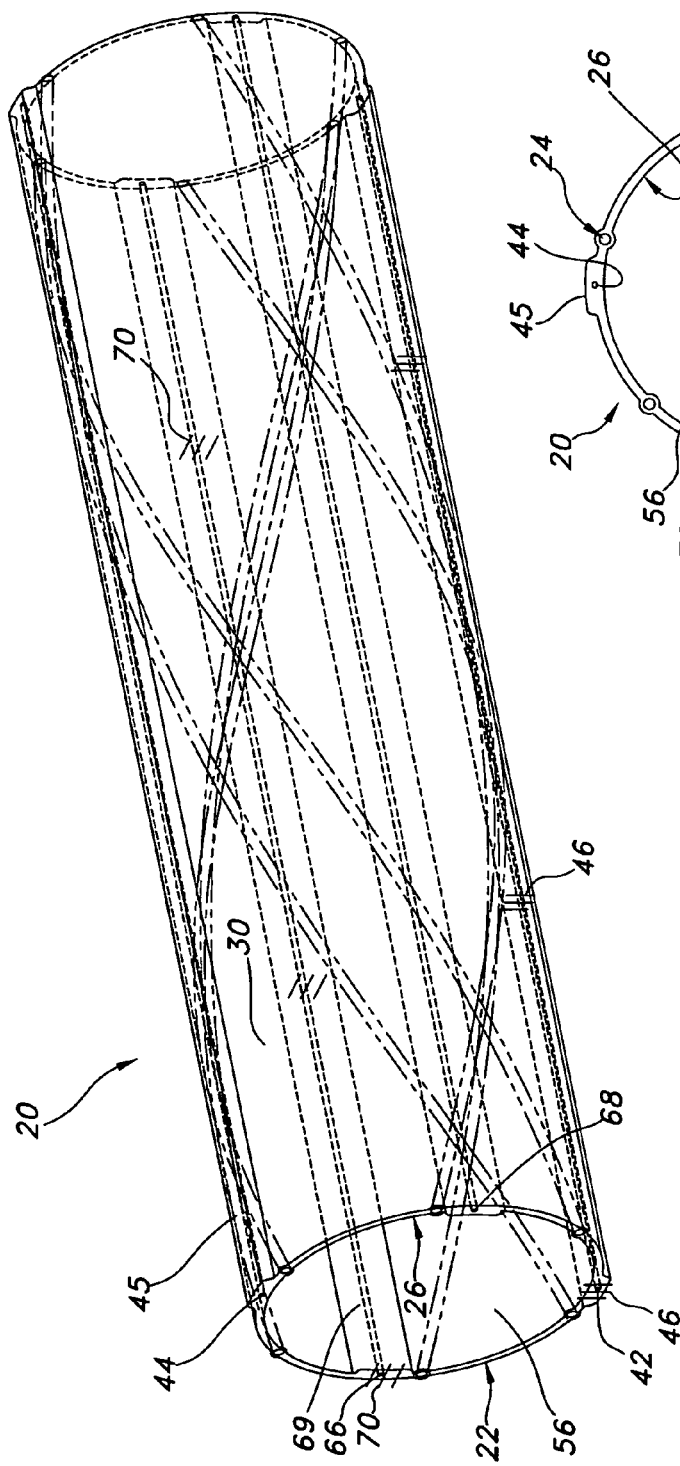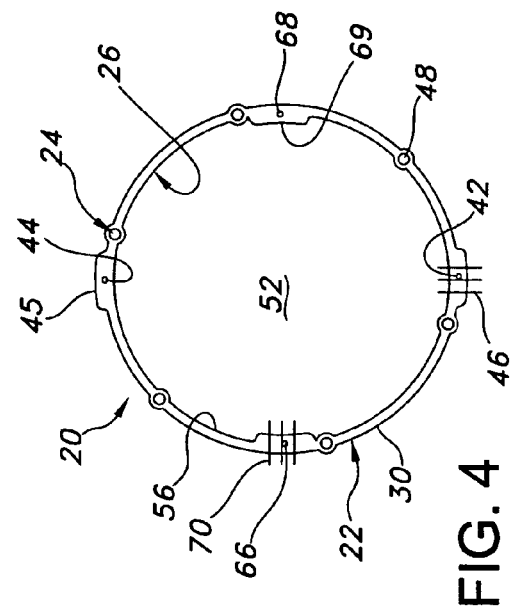
FIG. 3
FIG. 4

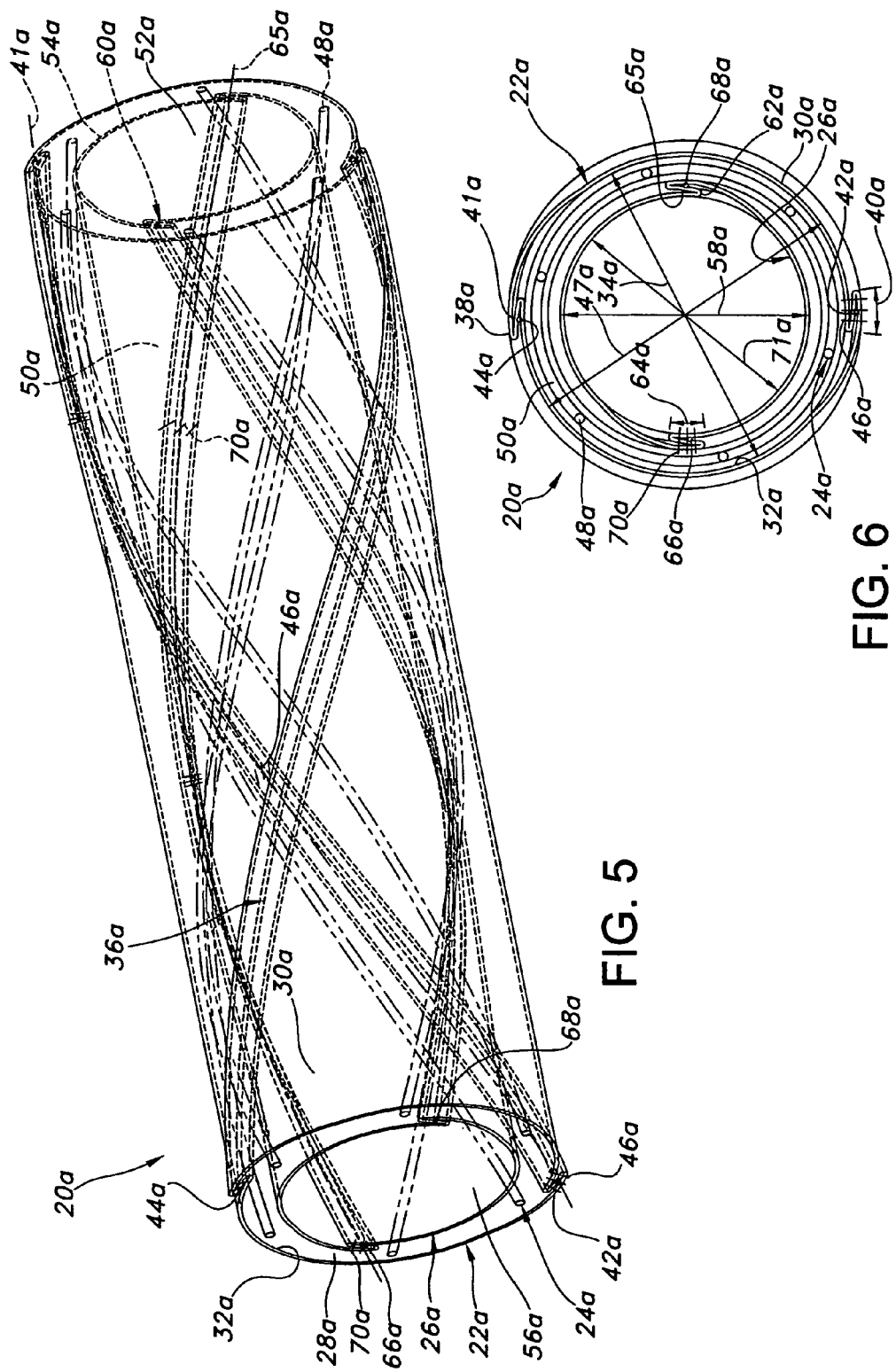

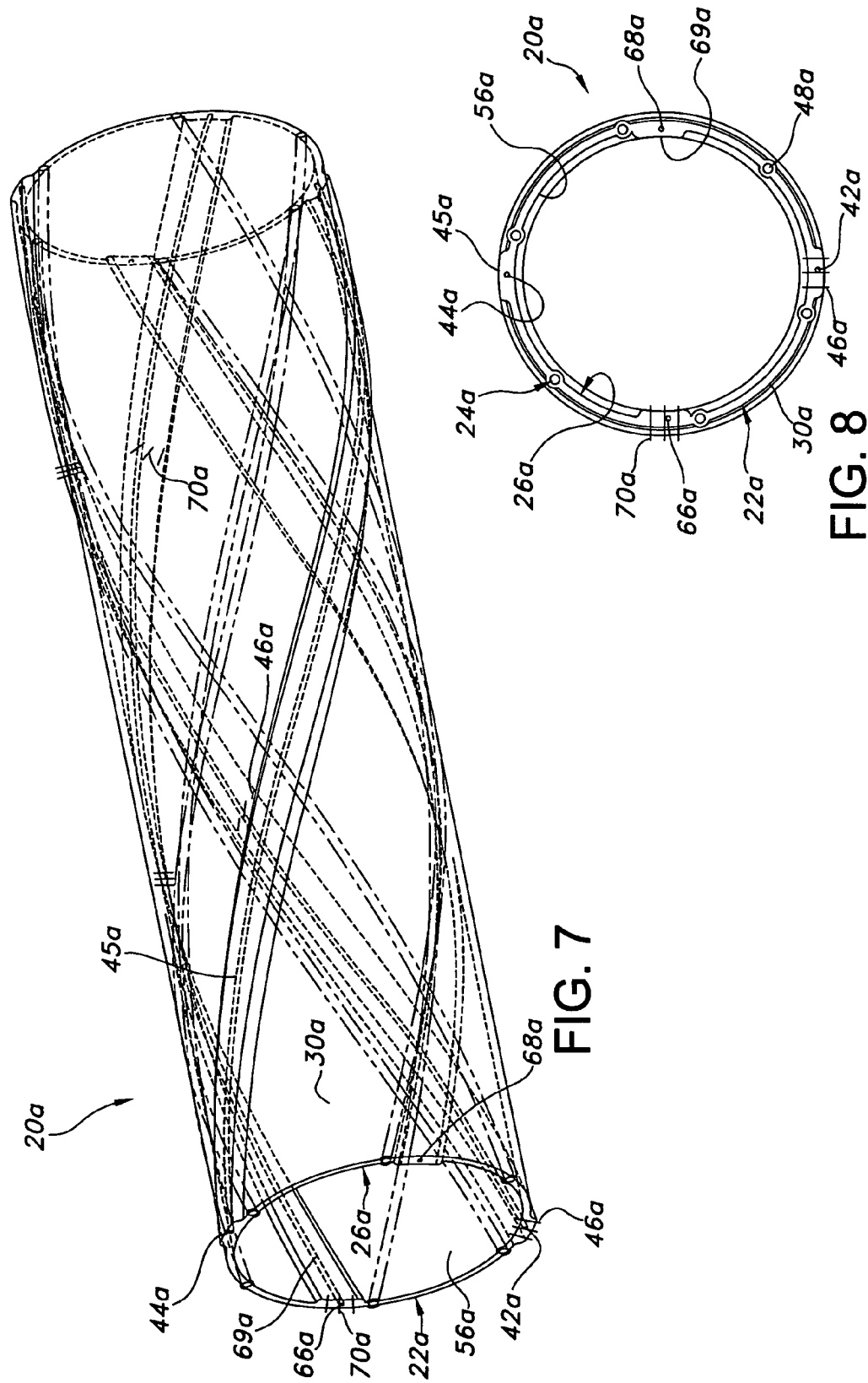

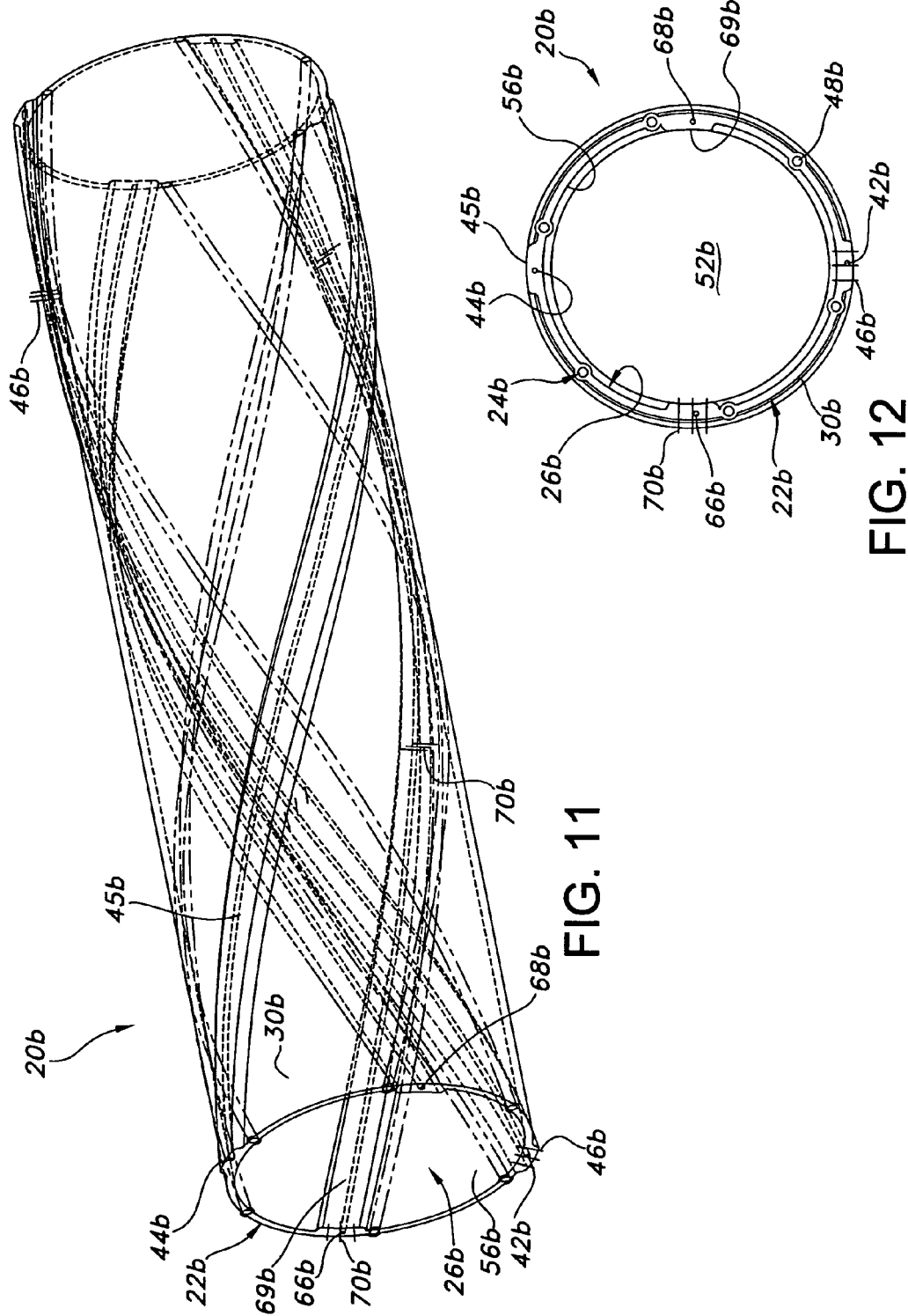

EPTFE LAMINATION—RESIZING EPTFE TUBING

FIELD OF THE INVENTION

The present invention relates to a vascular graft and, more specifically, to a vascular graft having a vessel structure and a pleat structure for varying the size of the vessel structure to fit the size of one or more additional structures, such as a stent, to which the vessel structure is assembled, and to a method for making such a vascular graft.

BACKGROUND OF THE INVENTION

It is well known to use extruded tube structures of polytetrafluoroethylene (PTFE) as implantable intraluminal prostheses, particularly for the vessel structures of vascular grafts. PTFE is particularly suitable as an implantable prosthesis as it exhibits superior biocompatibility. PTFE tube structures may be used for the vessel structures of vascular grafts in the replacement, repair of or supplement to a blood vessel as PTFE exhibits excellent mechanical properties and low thrombogenicity. In vascular applications, the vessel structures are manufactured from expanded polytetrafluoroethylene (ePTFE) tube structures. These tube structures have a microporous structure which allows natural tissue in-growth and cell endothelization once implanted in the vascular system. This contributes to long-term healing and patency of the graft. Vessel structures formed of ePTFE have a fibrous state which is defined by the interspaced nodes interconnected by elongated fibrils. Vessel structures formed of ePTFE having very small transverse dimensions, such as outer and inner diameters and wall thicknesses, are particularly well-suited for certain applications, such as the implantation in blood vessels, or replacement thereof, in humans.

The vessel structures of vascular grafts are frequently advantageously assembled with other vessel structures or stents. Such assemblies may provide for a vessel structure to be within another vessel structure or stent, or for the stent to be within the vessel structure. In such assemblies, it is typically preferable for the inner transverse dimension of the outer structure, such as the inner diameter of a vessel structure, to be generally the same as or slightly larger than the outer transverse dimension of the inner structure, such as a stent. Such correspondence between the inner and outer dimensions of the outer and inner structures results in the inner and outer surfaces thereof contacting one another in flush relation. This facilitates a flush, tight fit between the outer and inner structures which is normally preferred where at least one of the structures is a vessel structure of a vascular graft.

Such close correspondence between the inner and outer dimensions of the outer and inner structures may be provided by holding one or more of the inner and outer surfaces which are to be contiguous to very small tolerances during fabrication. Such precision is normally difficult, particularly when one or more of the structures is a vessel structure of a vascular graft formed of ePTFE. Such difficulty is compounded when the ePTFE vessel structure has very small transverse dimensions, such as outer and inner diameters and wall thicknesses. Fabrication of ePTFE vessel structures having very small transverse dimensions is desirable, as such vessel structures are well-suited for certain applications, as described in the foregoing.

SUMMARY OF THE INVENTION

A vascular graft includes a structural member, such as a basis stent, which is covered inside and outside by tubular, polymeric vessel structures. The tubular vessel structures each have one or more pleats varying in width which adjust the diameters of the vessel structures to fit snugly inside and outside the structural member. The method for making vascular grafts of various diameters involves adjusting the pleat widths which, in turn, alters the diameters of the vessel structures to fit the structural members, such as basis stents, which have a wide range of diameters.

Altering the inner or outer diameter of the vessel structure by adjusting the width of the pleats has significant advantages. First, vessel structures having a relatively few sizes can be fit to a relatively large range of diameters of structural members to create several diameters of vascular grafts.

A second advantage of adjusting pleat widths to assemble vascular grafts is that the diameter of the inner or liner vessel structure can be formed such that there is minimal clearance required for placing the basis stent or other structural member over it. Then, the outer or cover vessel structure can be placed over the basis stent and pleats formed to bring its diameter into contact with the basis stent. When pressure and heat are applied to the assembly, the vessel structures unite about the basis stent to form the vascular graft.

These and other features of the invention will be more fully understood from the following description of specific embodiments of the invention taken together with the accompanying drawings.

BRIEF DESCRIPTION OF THE DRAWINGS

In the drawings:

FIG. 1 is a perspective view of a vascular graft of the present invention, the graft being shown as having cover and liner vessel structures, longitudinal pleat structures and a stent structure before lamination thereof;

FIG. 2 is a left end elevation view of the vascular graft of FIG. 1;

FIG. 3 is a perspective view of the vascular graft of FIG. 1, the graft being shown after lamination of the cover and liner vessel structures, longitudinal pleat structures and stent structure;

FIG. 4 is a left end elevation view of the vascular graft of FIG. 3;

FIG. 5 is a perspective view of an alternative embodiment of the vascular graft of FIG. 1, the graft being shown as having cover and liner vessel structures, helical pleat structures which have the same rotational orientation, and a stent structure before lamination thereof;

FIG. 6 is a left end elevation view of the vascular graft of FIG. 5;

FIG. 7 is a perspective view of the vascular graft of FIG. 5, the graft being shown after lamination of the cover and liner vessel structures, helical pleat structures and stent structure;

FIG. 8 is a left end elevation view of the vascular graft of FIG. 7;

FIG. 11 is a perspective view of the vascular graft of FIG. 9, the graft being shown after lamination of the cover and liner vessel structures, helical pleat structures and stent structure;

FIG. 12 is a left end elevation view of the vascular graft of FIG. 11;

Corresponding reference characters indicate corresponding parts throughout the several views of the drawings.

DETAILED DESCRIPTION OF THE INVENTION

Figures 9, 10:
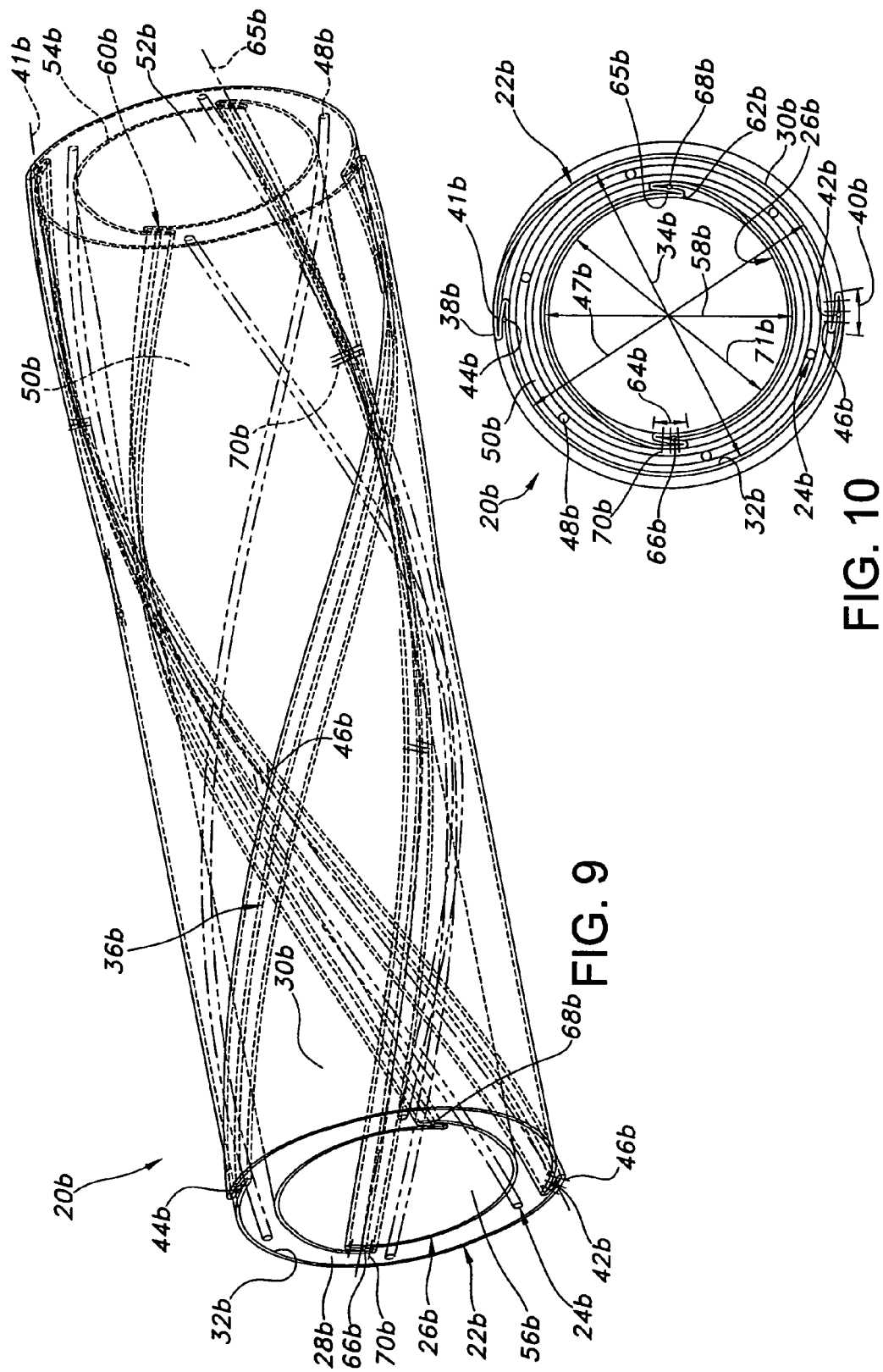
FIG. 9 is a perspective view of an alternative embodiment of the vascular graft of FIG. 1, the graft being shown as having cover and liner vessel structures, helical pleat structures which have opposite rotational orientations, and a stent structure before lamination thereof.
FIG. 10 is a left end elevation view of the vascular graft of FIG. 5.

Referring to the drawings and more particularly to FIGS. 1 and 2, a vascular graft 20 is shown for implantation within a body. The vascular graft 20 includes a cover vessel structure 22, stent structure 24, and liner vessel structure 26. The liner vessel structure 26 is within the stent structure 24 in coaxial relation therewith, and the stent structure 24 is within the cover vessel structure 22 in coaxial relation therewith.

The cover vessel structure 22 is elongate and has a lumen 28. The cover vessel structure 22 has outer and inner wall surfaces 30, 32 and is formed of expanded polytetrafluoroethylene (ePTFE) material. The cover vessel structure 22 has an annular cross-section which has an inner transverse dimension defined by an inner diameter 34. In alternative embodiments, the cross-section of the cover vessel structure 22 may be non-annular, such as by being rectangular.

The vascular graft 20 has one or more fold structures 36 which are integral with and extend from the outer wall surface 30 of the cover vessel structure 22. One embodiment of the fold structures 36 are pleat structures 38 which are formed by drawing together adjacent portions of the inner wall surface 32 into abutting relation with one another. Formation of the pleat structures 38 results in the reduction of the inner diameter 34 of the cover vessel structure 22. The pleat structures 38 each have a transverse length 40 which is related to the inner diameter 34 such that increasing the transverse length causes a decrease in the inner diameter 34. This provides for the alteration of the inner diameter 34 to specific sizes. The range of sizes to which the inner diameter 34 may be altered may be limited in a possible embodiment of the cover vessel structure 22.

The pleat structures 38 each overlap the outer wall surface 30. The pleat structures 38 each have a center which is intersected by a corresponding pleat axis 41 such that the pleat axes each intersect a transverse plane of the cover vessel structure 22. The pleat structures 38 are each oriented relative to the cover vessel structure 22 such that the pleat axes 41 each have a longitudinal orientation relative thereto.

The vascular graft 20 includes one or more radio-opaque markers 42 which are located within the pleat structures 38, as shown in FIG. 2. Alternatively, or in addition to the markers 42, the vascular graft 20 includes one or more radio-opaque markers 44 which are located between the pleat structures 38 and outer wall surface 30. The markers 42, 44 have a relatively small cross-sectional area. The markers 42, 44 have a length which may be relatively short. Alternatively, the markers 42, 44 may have a substantial length and extend longitudinally relative to the cover vessel structure 22. The markers 42, 44 which have a substantial length may have indications thereon to signify the longitudinal position thereof.

The pleat structures 38 are secured to the outer wall surface 30, such as by being laminated thereto. Lamination results from heating and applying pressure to the pleat structures 38 and cover vessel structure 22 such that the pleat structures are fused to the outer wall surface 30. Such fusing typically has, at most, a neglible effect on the contour of the outer wall surface 30. For example, the lamination of the pleat structures 38 to the outer wall surface 30 may result in the formation of elongate steps 45 or wrinkles thereon such that the steps or wrinkles correspond to respective pleat structures. Such steps 45, wrinkles, or other changes in the outer wall surface 30 resulting from the lamination are sufficiently small as to have an insubstantial effect on the outer diameter 47 of the cover vessel structure 22. After the lamination of the pleat structures 38 to the outer wall surface 30, the outer diameter 47 is generally uniform. Consequently, formation of the pleat structures 38 and lamination thereof to the outer wall surface 30 results in the reduction of the outer diameter 47. Alternatively, or in addition to the lamination, the pleat structures 38 may each be secured to the outer wall surface 30 by being sutured thereto by suture material such as suture thread 46.

Securing the pleat structures 38 to the outer wall surface 30 fixes the radio-opaque markers 42, 44 to the cover vessel structure 22 such that relative displacement between the markers and cover vessel structure is obstructed. Consequently, the position of the cover vessel structure 22 after implantation thereof in a body may be determined by x-ray, CAT scan, MRI, or fluoroscopy by visualizing the radio-opaque markers 42, 44.

The stent structure 24 includes a plurality of elongate structural members 48 which may form a wire-mesh tube. The stent structure 24 has at least one transverse aperture 50 between the structural members 48. Preferably, the structural members 48 are separated by numerous transverse apertures 50 throughout the stent structure 24. The stent structure 24, including the structural members 48, may be formed of materials such as nitinol, elgiloy, stainless steel or cobalt chromium, including NP35N. Additionally, the stent structure 24, including the structural members 48, may be formed of materials such as stainless steel, platinum, gold, titanium and other biocompatible metals, as well as polymeric stents. Also, the stent structure 24, including the structural members 48, may be formed of materials including cobalt-based alloy such as Elgiloy, platinum, gold, titanium, tantalum, niobium, and combinations thereof and other biocompatible materials, as well as polymers. Additionally, the structural members 48 or portions thereof may have an inner core formed of tantalum gold, platinum, iridium, or a combination thereof, and an outer cladding of nitinol to provide composite members for improved radio-opacity or visibility. Examples of such composite members are disclosed in U.S. Patent Application Publication 2002/0035396, the entire contents of which are hereby incorporated by reference herein.

The stent structure 24 may have various embodiments. For example, the stent structure 24 may be self-expanding or expandable by a balloon. The stent structure 24 may include one or more coiled stainless steel springs, helically wound coil springs including a heat-sensitive material, or expanding stainless steel stents formed of stainless steel wire in a zig-zag pattern. The stent structure 24 may be capable of radially contracting or expanding, such as by radial or circumferential distension or deformation. Self-expanding stents include stents which mechanically urge the stent to radially expand, and stents which expand at one or more specific temperatures as a result of the memory properties of the stent material for a specific configuration. Nitinol is a material which may be included in the stent structure 24 for providing radial expansion thereof both by mechanical urging, or by the memory properties of the nitinol based on one or more specific temperatures. The stent structure 24 may include one or more of the stents disclosed in U.S. Pat. Nos. 4,503,569, 4,733,665, 4,856,516, 4,580,568, 4,732,152, and 4,886,062, the entire contents of each of which are hereby incorporated by reference herein.

The stent structure 24 may include material which is radio-opaque. Consequently, the position of the stent structure 24 after implantation thereof in a body may be determined by x-ray, CAT scan, MRI, or fluoroscopic procedures. Alternatively, the stent structure 24 may be formed entirely of material, such as some polymers, which is not detectable from x-ray, CAT scan, MRI, or fluoroscopy, and is not visible in radiographic procedures.

The liner vessel structure 26 is elongate and has a lumen 52 for carrying fluids, such as blood. The liner vessel structure 26 has outer and inner wall surfaces 54, 56 and is formed of ePTFE material. The liner vessel structure 26 has an annular cross-section which has outer transverse dimension defined by an outer diameter 58. In alternative embodiments, the cross-section of the liner vessel structure 26 may be non-annular, such as by being rectangular.

The vascular graft 20 has one or more fold structures 60 which are integral with and extend from the inner wall surface 56 of the liner vessel structure 26. One embodiment of the fold structures 60 are pleat structures 62 which are formed by drawing together adjacent portions of the outer wall surface 54 into abutting relation with one another. Formation of the pleat structures 62 results in the reduction of the outer diameter 58 of the liner vessel structure 26. The pleat structures 62 each have a transverse length 64 which is related to the outer diameter 58 such that increasing the transverse length causes a decrease in the outer diameter 58. This provides for the alteration of the outer diameter 58 to specific sizes. The range of sizes to which the outer diameter 58 may be altered may be limited in a possible embodiment of the liner vessel structure 26.

The pleat structures 62 each overlap the inner wall surface 56. The pleat structures 62 each have a center which is intersected by a pleat axis 65 such that the pleat axes each intersect a transverse plane of the liner vessel structure 26. The pleat structures 62 are each oriented relative to the liner vessel structure 26 such that the pleat axes 65 each have a longitudinal orientation relative thereto.

The vascular graft 20 includes one or more radio-opaque markers 66 which are located within the pleat structures 62, as shown in FIG. 2. Alternatively, or in addition to the markers 66, the vascular graft 20 includes one or more radio-opaque markers 68 which are located between the pleat structures 62 and inner wall surface 56. The markers 66, 68 have a relatively small cross-sectional area. The markers 66, 68 have a length which may be relatively short. Alternatively, the markers 66, 68 may have a substantial length and extend longitudinally relative to the liner vessel structure 26. The markers 66, 68 which have a substantial length may have indications thereon to signify the longitudinal position thereof.

The pleat structures 62 are secured to the inner wall surface 56, such as by being laminated thereto. Lamination results from heating and applying pressure to the pleat structures 62 and liner vessel structure 26 such that the pleat structures are fused to the inner wall surface 56. Such fusing typically has, at most, a neglible effect on the contour of the inner wall surface 56. For example, the lamination of the pleat structures 62 to the inner wall surface 56 may result in the formation of elongate steps 69 or wrinkles thereon such that the steps or wrinkles correspond to respective pleat structures. Such steps 69, wrinkles, or other changes in the inner wall surface 56 resulting from the lamination are sufficiently small as to have an insubstantial effect on the inner diameter 71 of the liner vessel structure 26. After the lamination of the pleat structures 62 to the inner wall surface 56, the inner diameter 71 is generally uniform. Consequently, formation of the pleat structures 62 and lamination thereof to the inner wall surface 56 results in the reduction of the inner diameter 71. Alternatively, or in addition to the lamination, the pleat structures 62 may each be secured to the inner wall surface 56 by being sutured thereto by suture material such as suture thread 70.

Securing the pleat structures 62 to the inner wall surface 56 fixes the radio-opaque markers 66, 68 to the liner vessel structure 26 such that relative displacement between the markers and liner vessel structure is obstructed. Consequently, the position of the liner vessel structure 26 after implantation thereof in a body may be determined by x-ray, CAT scan, or MRI procedures.

The cover and liner vessel structures 22, 26 are arranged such that the pleat structures 38 alternate with the pleat structures 62, as shown in FIGS. 1 and 2. Consequently, each of the pleat structures 38 is between a pair of the pleat structures 62, and each of the pleat structures 62 is between a pair of the pleat structures 38, relative to the cross-sections of the vessel structures 22, 26.

The cover and liner vessel structures 22, 26 are secured to one another by lamination, as shown in FIGS. 3 and 4. Lamination results from heating and applying pressure to the cover and liner vessel structures 22, 26 such that the inner wall surface 32 is fused to the outer wall surface 54. A pathway for the lamination is provided by the transverse apertures 50 in the stent structure 24 into which the cover and liner vessel structures 22, 26 merge to fuse to one another. Additionally, the fusing of the portions of the cover and liner vessel structures 22, 26 which extend through the transverse apertures 50 fixes the stent structure 24 to the vessel structures and prevents movement of the stent structure relative thereto.

The cover and liner vessel structures 22, 26, and the respective integral fold structures 36, 60, are preferably formed of ePTFE. Alternatively, or in combination with ePTFE, the cover and liner vessel structures 22, 26, and the respective integral fold structures 36, 60, may be formed of biocompatible materials, such as polymers which may include fillers such as metals, carbon fibers, glass fibers or ceramics. Such polymers may include olefin polymers, polyethylene, polypropylene, polyvinyl chloride, polytetrafluoroethylene which is not expanded, fluorinated ethylene propylene copolymer, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polycarbonates, polyaldehydes, natural rubbers, polyester copolymers, styrene-butadiene copolymers, polyethers, such as fully or partially halogenated polyethers, copolymers, and combinations thereof. Also, polyesters, including polyethylene terephthalate (PET) polyesters, polypropylenes, polyethylenes, polyurethanes, polyolefins, polyvinyls, polymethylacetates, polyamides, naphthalane dicarboxylene derivatives, and natural silk may be included in the cover and liner vessel structures 22, 26, and the respective integral fold structures 36, 60.

The cover and liner vessel structures 22, 26, the respective integral fold structures 36, 60, and the stent structure 24 may be treated with anti-thrombogenic agents (such as heparin, heparin derivatives, urokinase, and PPack (dextrophenylalanine proline arginine chloromethylketone)), anti-proliferative agents (such as enoxaprin, angiopeptin, or monoclonal antibodies capable of blocking smooth muscle cell proliferation, hirudin, and acetylsalicylic acid), anti-inflammatory agents (such as dexamethasone, prednisolone, corticosterone, budesonide, estrogen, sulfasalazine, and mesalamine), antineoplastic/antiproliferative/anti-miotic agents (such as paclitaxel, 5-fluorouracil, cisplatin, vinblastine, vincristine, epothilones, endostatin, angiostatin and thymidine kinase inhibitors), anesthetic agents (such as lidocaine, bupivacaine, and ropivacaine), anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides), vascular cell growth promotors (such as growth factor inhibitors, growth factor receptor antagonists, transcriptional activators, and translational promotors), vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin), cholesterol-lowering agents, vasodilating agents, and agents which interfere with endogenous vascoactive mechanisms.

The cover vessel structure 22, fold structures 36, pleat structures 38, and markers 42, 44 may be formed and assembled separately and apart from the stent structure 24 and liner vessel structure 26. Also, the liner vessel structure 26, fold structures 60, pleat structures 62, and markers 66, 68 may be formed and assembled separately and apart from the stent structure 24 and cover vessel structure 22. Following such separate formations and assemblies, the cover and liner vessel structures 22, 26, including the corresponding fold structures 36, 60, pleat structures 38, 62, and markers 42, 44, 66, 68 may be arranged and assembled as shown in FIGS. 1 and 2.

An alternative embodiment of the vascular graft 20a is shown in FIGS. 5 to 8. FIGS. 5 to 8 are views which correspond to the views of FIGS. 1 to 4, respectively. Parts shown in FIGS. 5 to 8 which correspond to parts shown in FIGS. 1 to 4 have the same reference numeral as in FIGS. 1 to 4 with the addition of the suffix "a" in FIGS. 5 to 8. A difference between the vascular grafts 20a, 20 is that the pleat axes 41a, 65a each have a helical orientation relative to the cover and liner vessel structures 22a, 26a. The helical orientations of the pleat axes 41a, 65a each have a rotational orientation relative to the cover and liner vessel structures 22a, 26a such that the rotational orientations are the same.

An alternative embodiment of the vascular graft 20b is shown in FIGS. 9 to 12. FIGS. 9 to 12 are views which correspond to the views of FIGS. 1 to 4, respectively. Parts shown in FIGS. 9 to 12 which correspond to parts shown in FIGS. 1 to 4 have the same reference numeral as in FIGS. 1 to 4 with the addition of the suffix "b" in FIGS. 9 to 12. A difference between the vascular grafts 20b, 20 is that the pleat axes 41b, 65b each have a helical orientation relative to the cover and liner vessel structures 22b, 26b. The helical orientations of the pleat axes 41b, 65b each have a rotational orientation relative to the cover and liner vessel structures 22b, 26b such that the rotational orientations are opposite.

Figure 13:
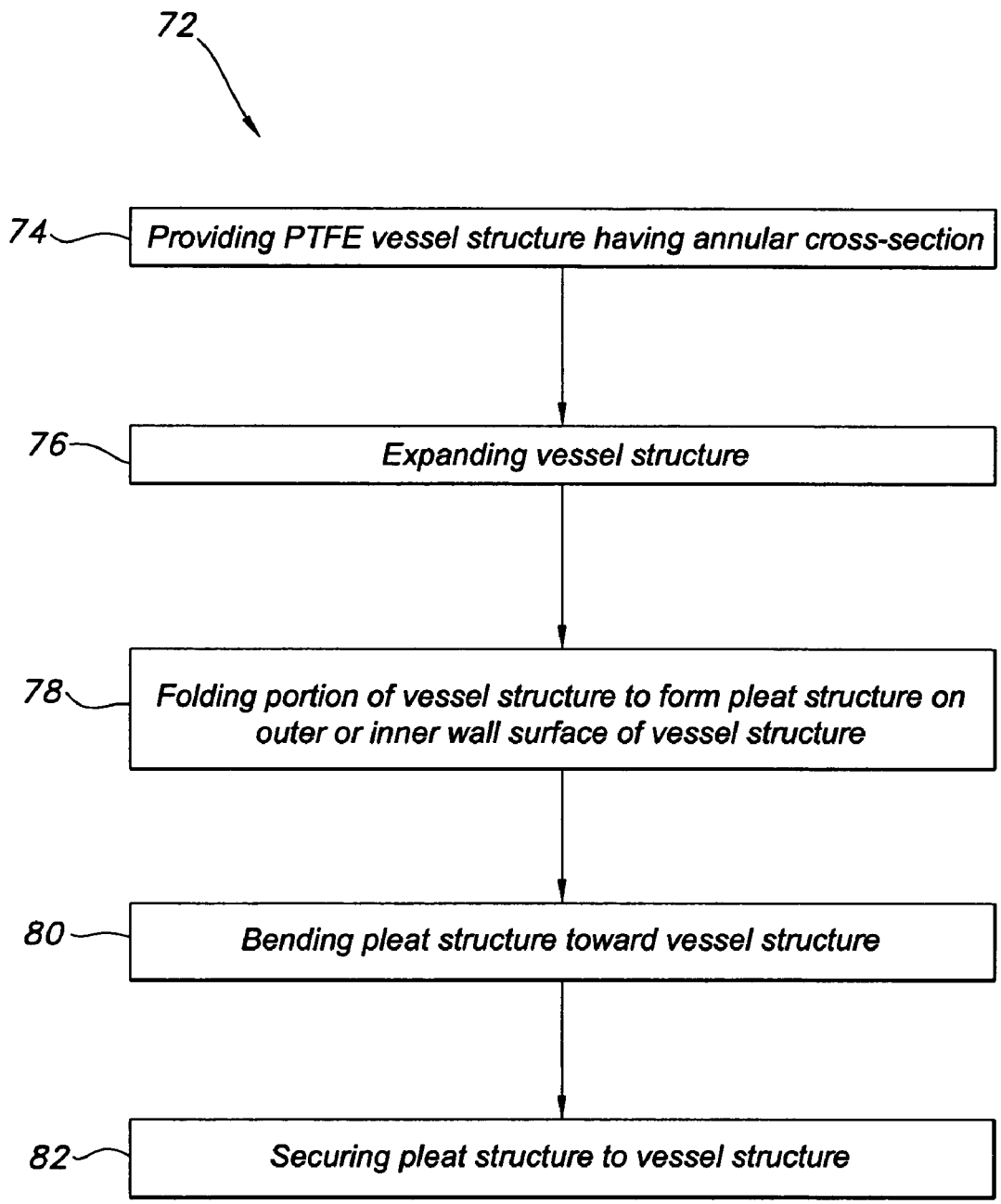
FIG. 13 is a block diagram of a method of the present invention for making the cover and liner vessel structure of FIG. 1, the method providing for the formation of pleat structures on the outer or inner wall surfaces of the vessel structures.

A method 72 for making the vascular graft 20, 20a, 20b is shown in the block diagram of FIG. 13. The method 72 includes providing 74 a vessel structure which is formed of pliable PTFE material and has an annular cross-section. The vessel structure is longitudinally expanded 76.

Following the expansion 76, one or more portions of the vessel structure are folded 78 such that adjacent portions of the inner or outer wall surface of the vessel structure are drawn together into abutting relation to one another. The folding 78 produces one or more pleat structures which are integral with the vessel structure.

The folding 78 of the vessel structure such that the inner wall surface is drawn together produces one or more pleat structures which extend from the outer wall surface of the vessel structure, such as the pleat structures 38, 38a, 38b of the cover vessel structure 22, 22a, 22b. Alternatively, the folding 78 of the vessel structure such that the outer wall surface is drawn together produces one or more pleat structures which extend from the inner wall surface of the vessel structure, such as the pleat structures 62, 62a, 62b of the liner vessel structure 26, 26a, 26b. The pleat structures produced by the folding 78 may have a various orientations relative to the vessel structure, such as longitudinal or helical as illustrated in FIGS. 1, 5, and 9.

Following the folding 78, the one or more pleat structures are bent 80 toward the outer or inner wall surface of the vessel structure to overlap the pleat structure onto the outer or inner wall surface. The bending 80 provides for the one or more pleat structures which extend from the outer wall surface to be bent toward the outer wall surface, such as the pleat structures 38, 38a, 38b of the cover vessel structure 22, 22a, 22b illustrated in FIGS. 1, 2, 5, 6, 9, and 10. Alternatively, the one or more pleat structures which extend from the inner wall surface are bent 80 toward the inner wall surface, such as the pleat structures 62, 62a, 62b of the liner vessel structure 26, 26a, 26b.

Following the bending 80, the one or more pleat structures are secured 82 to the outer or inner wall surface, such as by suturing or lamination. The one or more pleat structures which extend from the outer wall surface are secured 82 to the outer wall surface, such as the pleat structures 38, 38a, 38b of the cover vessel structure 22, 22a, 22b illustrated in FIGS. 1, 2, 5, 6, 9, and 10. Alternatively, the one or more pleat structures which extend from the inner wall surface are secured 82 to the inner wall surface, such as the pleat structures 62, 62a, 62b of the liner vessel structure 26, 26a, 26b.

A vessel structure which is made according to the method 72 may be implanted in the body of a patient as a single vessel structure, or may be assembled to a stent structure. Additionally, a vessel structure which is made according to the method 72, in which the one or more pleat structures extends from the outer wall surface of the vessel structure may be used as a cover vessel structure, such as the cover vessel structure 22, 22a, 22b, of a vascular graft which includes a stent structure and liner vessel structure. Further, a vessel structure which is made according to the method 72, in which the one or more pleat structures extends from the inner wall surface of the vessel structure may be used as a liner vessel structure, such as the liner vessel structure 26, 26a, 26b, of a vascular graft which includes a stent structure and liner vessel structure.

Figure 14:
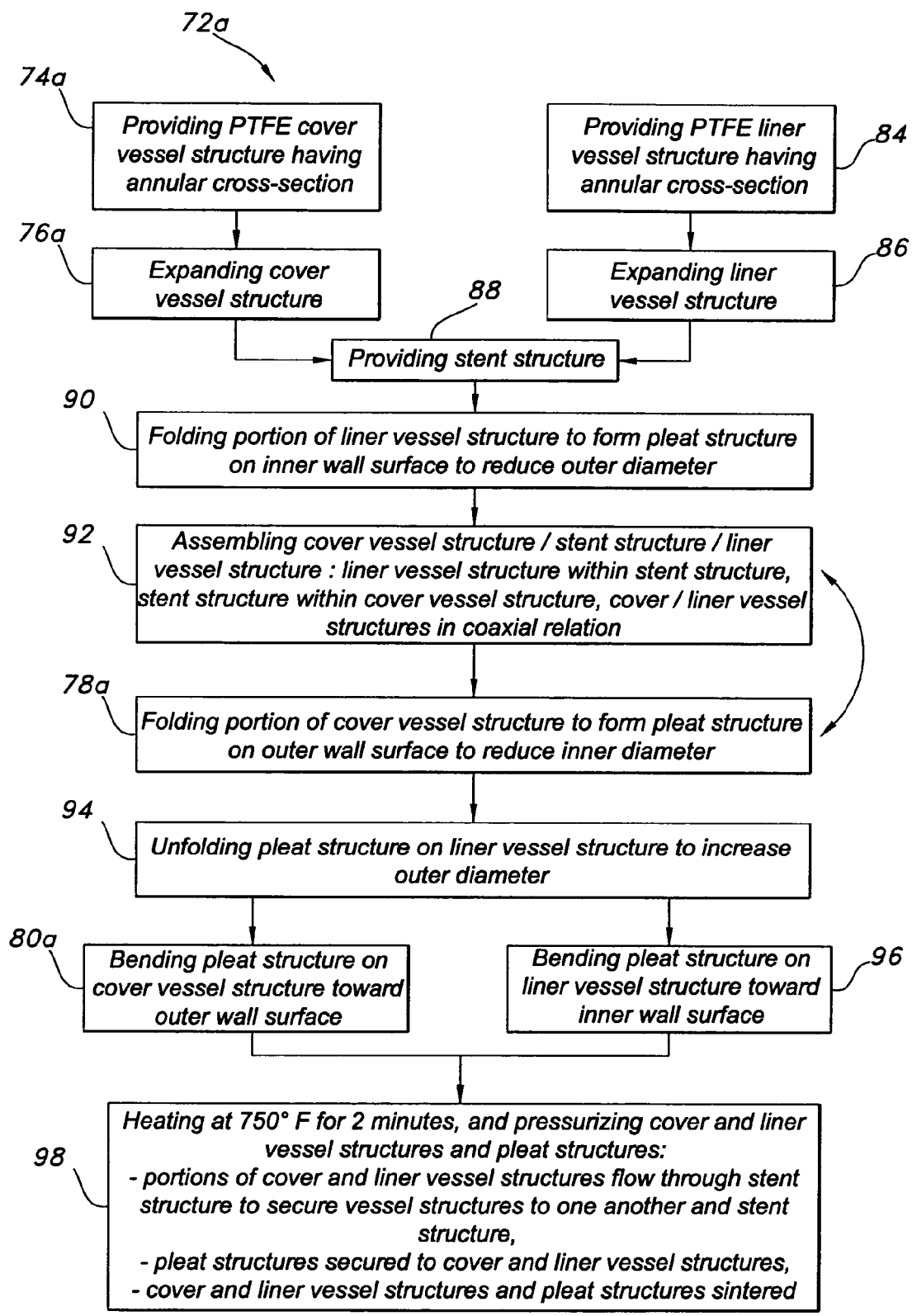
FIG. 14 is a block diagram of a method of the present invention for making the vascular graft of FIGS. 3, 7 and 11, the method providing for the assembly of the stent structure between the cover and liner vessel structures and the formation of pleat structures thereon.

An alternative embodiment of the method 72a is shown in FIG. 14. Steps shown in FIG. 14 which correspond to steps shown in FIG. 13 have the same reference numeral as in FIG. 13 with the addition of the suffix "a" in FIG. 14. The method 72a includes providing 74a a cover vessel structure which is formed of pliable PTFE material and has an annular cross-section. The method 72a further includes providing 84 a liner vessel structure which is formed of pliable PTFE material and has an annular cross-section. The cover and liner vessel structures are longitudinally expanded 76a, 86, respectively. The method 72a includes providing 88 a stent structure.

Following the expansions 76a, 86, one or more portions of the liner vessel structure are folded 90 such that adjacent portions of the outer wall surface of the vessel structure are drawn together into abutting relation to one another. The folding 90 produces one or more pleat structures which are integral with the liner vessel structure and extend from the inner wall surface thereof, such as the pleat structures 62, 62a, 62b of the liner vessel structure 26, 26a, 26b illustrated in FIGS. 2, 6, and 10. The one or more pleat structures produced by the folding 90 may have a various orientations relative to the vessel structure, such as longitudinal or helical as illustrated in FIGS. 1, 5, and 9.

The cover vessel structure is assembled 92 to the stent structure such that the stent structure is within the cover vessel structure. The liner vessel structure is assembled 92 to the stent structure such that the liner vessel structure is within the stent structure. The assembly 92 provides for the cover and liner vessel structures to be arranged in coaxial relation.

The assembly 92 of the liner vessel structure and stent structure preferably follows the folding 90, as depicted in FIG. 14, because the folding 90 results in a reduction of the outer diameter of the liner vessel structure. This provides a transverse clearance between the liner vessel structure and stent structure which facilitates relative longitudinal displacement between the stent and liner vessel structure. Such relative longitudinal displacement is typical during the assembly 92 to longitudinally position the liner vessel structure within the stent structure.

Following the assembly 92, one or more portions of the cover vessel structure are folded 78a such that adjacent portions of the inner wall surface of the vessel structure are drawn together into abutting relation to one another. The folding 78a produces one or more pleat structures which are integral with the cover vessel structure and extend from the outer wall surface thereof, such as the pleat structures 38, 38a, 38b of the cover vessel structure 22, 22a, 22b. The one or more pleat structures produced by the folding 78a may have a various orientations relative to the vessel structure, such as longitudinal or helical.

The folding 78a of the cover vessel structure after the assembly 92 thereof to the stent structure provides the advantage of using a cover vessel structure having an inner diameter which is greater than the outer transverse dimension of the stent structure. This provides a transverse clearance between the stent structure and cover vessel structure which facilitates relative longitudinal displacement between the stent and cover vessel structure. This is typical during the assembly 92 to longitudinally position the stent structure within the liner vessel structure.

The folding 78a of such a cover vessel structure after assembly 92 thereof to the stent structure reduces the inner diameter of the cover vessel structure which provides for inward displacement of the inner wall surface thereof. Such inward displacement results in the inner wall surface of the cover vessel structure moving into abutting relation with the outer surface of the stent structure which is within the cover vessel structure. The inward displacement of the inner wall surface of the cover vessel structure is limited by the engagement thereof with the outer surface of the stent structure as a result of the relatively greater stiffness and strength of the stent structure.

The folding 78a provides for the reduction of the inner diameter of the cover vessel structure to different dimensions by varying the number of pleat structures and the transverse lengths thereof, such as the transverse lengths 40, 40a, 40b. This provides for a cover vessel structure to have a flush, tight fit with stent structures having different outer transverse dimensions because the inner diameter of the cover vessel structure may be adjusted to match the various outer transverse dimensions of the stent structures. Additionally, the precision of the inner diameter of the fabricated cover vessel structure, prior to the folding 78a, is not as demanding provided that such inner diameter is greater than the outer transverse dimension of the stent structure since the inner diameter may be reduced by the folding 78a to provide the flush, tight fit with the stent structure.

Alternatively, the folding 78a may preceded the assembly 92 of the cover vessel structure and stent structure, as depicted in FIG. 14. Such folding 78a which precedes the assembly 92 may be in addition to or instead of the folding 78a described in the foregoing which precedes the assembly 92.

Following the assembly 92, the one or more pleat structures extending from the liner vessel structure are unfolded 94. This increases the outer diameter of the liner vessel structure which provides for outward displacement of the outer wall surface thereof. Such outward displacement results in the outer wall surface of the liner vessel structure moving into abutting relation with the inner surface of the stent structure within which the liner vessel structure is located. The outward displacement of the outer wall surface of the liner vessel structure is limited by the engagement thereof with the inner surface of the stent structure as a result of the relatively greater stiffness and strength of the stent structure.

The unfolding 94 provides for the increase of the outer diameter of the liner vessel structure to different dimensions by varying the number of pleat structures and the transverse lengths thereof, such as the transverse lengths 64, 64a, 64b. This provides for a liner vessel structure to have a flush, tight fit with stent structures having different inner transverse dimensions because the outer diameter of the liner vessel structure may be adjusted to match the various outer transverse dimensions of the stent structures. Additionally, the precision of the outer diameter of the fabricated inner vessel structure, prior to the folding 90, is not as demanding provided that such outer diameter is greater than the inner transverse dimension of the stent structure since the outer diameter may be reduced by the folding 90 and unfolded 94 to provide the flush, tight fit with the stent structure.

Following the unfolding 94, the one or more pleat structures which extend from the cover vessel structure are bent 80a toward the outer wall surface thereof to overlap the one or more pleat structures onto the outer wall surface. Examples of the pleat structures following the bending 80a are the pleat structures 38, 38a, 38b of the cover vessel structure 22, 22a, 22b illustrated in FIGS. 1, 2, 5, 6, 9, and 10.

Also following the unfolding 94, the one or more pleat structures which extend from the liner vessel structure are bent 96 toward the inner wall surface thereof to overlap the one or more pleat structures onto the inner wall surface. Examples of the pleat structures following the bending 96 are the pleat structures 62, 62a, 62b of the liner vessel structure 26, 26a, 26b.

Examples of the cover vessel structure, stent structure and liner vessel structure following the folding 90, assembly 92, folding 78a, unfolding 94, and bending 80a, 96 are included in the vascular grafts 20, 20a, 20b shown in FIGS. 1, 2, 5, 6, 9, and 10.

Following the bending 80a, 96, the assembly, including the cover vessel structure, stent structure and liner vessel structure, are heated and subjected to increased pressure to secure the structures together by lamination 98. The lamination 98 causes portions of the cover and liner vessel structures to merge in or through the transverse apertures in the stent structure such that the cover and liner vessel structures are fused to one another. The fusing provides for the securing together of the cover and liner vessel structures. Additionally, the fusing of the portions of the cover and liner vessel structures which extend through the transverse apertures fixes the stent structure to the vessel structures and prevents movement of the stent structure relative thereto.

The lamination 98 also provides for the fusing of the pleat structures to the corresponding outer or inner wall surfaces to secure the pleat structures to the respective cover or liner vessel structures. Instead of or in addition to the lamination 98, the pleat structures may be secured to the corresponding cover or liner vessel structures by being sutured to the outer or inner wall surfaces by a suture material such as suture thread.

The heating and increased pressure which produce the lamination process 98 may also provide for sintering 98 of the cover and liner vessel structures and pleat structures. For example, heating the cover and liner vessel structures and pleat structures at a temperature of 750 degrees F. for a duration of 2 minutes will provide simultaneous lamination and sintering 98 of the cover and liner vessel structures and pleat structures.

While the invention has been described by reference to certain preferred embodiments, it should be understood that numerous changes could be made within the spirit and scope of the inventive concept described. Accordingly, it is intended that the invention not be limited to the disclosed embodiments, but that it have the full scope permitted by the language of the following claims.

What is claimed is:

1. A vascular graft having a lumen therethrough, the graft comprising:
    a vessel structure having a first layer of material disposed about the circumference of the vessel structure, a second layer of material disposed about the circumference of the vessel structure,
    a stent structure within the vessel structure,
    the vessel structure including a plurality of pleat structures including a first pleat structure, a second pleat structure, and a third pleat structure, the first and third pleat structure formed of one of the first or second layers of material and the second pleat structure formed of the other layer of material,
    the first, second, and third pleat structures each being in the form of a first turn-back of said same layer of material followed by a second opposing turn-back of said same layer of material,
    the first layer of material, second layer of material, and stent structure being secured to one another such that relative displacement between the stent structure and the first layer of material and second layer of material is obstructed,
    wherein the first and third pleat structures are circumferentially offset from one another, and
    wherein the first, second, and third pleat structures are each oriented helically relative to the longitudinal axis of the vascular graft; the first and third pleat structures having an opposite rotational orientation as compared with the second pleat structure.

2. A vascular graft according to claim 1, wherein said vascular graft further comprises a suture material, said first and second pleat structures being sutured to said first or second layer of material.

3. A vascular graft according to claim 1, wherein the vessel structure is free of pleat structures circumferentially between the first and third pleat.

4. A vascular graft according to claim 1, and further comprising a radio-opaque marker within said first or second pleat structures and secured thereto.

5. A vascular graft according to claim 1, and further comprising a radio-opaque marker positioned between said first or second pleat structures and said first or second layer of material, said radio-opaque marker being secured to said first or second pleat structure or said first or second layer of material.

6. A vascular graft according to claim 1, wherein said vessel and first and second pleat structures comprise a PTFE material which is expanded.

7. A vascular graft according to claim 1, wherein said stent structure has a transverse aperture into which said first layer of material or second layer of material extends for merging of said first layer of material and said second layer of material to one another to provide said securing of said first layer of material and said second layer of material and stent structure to one another.

8. A vascular graft according to claim 1 further comprising a radio-opaque marker within the first, second, and third pleat structures and secured thereto.

9. A vascular graft according to claim 1 further comprising a fourth pleat structure formed of the second layer of material, the fourth pleat structure being circumferentially offset from the second pleat structure, the fourth pleat structure being in the form of a first turn-back of the same layer of material followed by a second opposing turn-back of the same layer of material.

10. A vascular graft according to claim 1 wherein the first layer of material and the second layer of material include fillers selected from the group consisting of metals, carbon fibers, glass fibers, and ceramics.

* * * * *